United States Patent
Coon et al.

(10) Patent No.: US 7,172,596 B2
(45) Date of Patent: Feb. 6, 2007

(54) MINIMALLY INVASIVE TOTAL KNEE ARTHROPLASTY METHOD AND INSTRUMENTATION

(76) Inventors: Thomas M. Coon, 3782 Siskiyou St., Redding, CA (US) 96001; Alfred J Tria, Jr., 210 Brooks Rd., Princeton, NJ (US) 08540; Donald M. Smucker, 27889 White Rd., Perrysburg, OH (US) 43551; Richard R. Van Zile, 03092 C.R. 16, Bryan, OH (US) 43506

( * ) Notice: Subject to any disclaimer, the term of this patent is extended or adjusted under 35 U.S.C. 154(b) by 173 days.

(21) Appl. No.: 10/377,068

(22) Filed: Feb. 28, 2003

(65) Prior Publication Data

US 2003/0171757 A1    Sep. 11, 2003

Related U.S. Application Data

(60) Provisional application No. 60/361,990, filed on Mar. 5, 2002.

(51) Int. Cl.
*A61F 5/00* (2006.01)
*A61B 17/58* (2006.01)

(52) U.S. Cl. .......................................... 606/87; 606/88
(58) Field of Classification Search ........... 606/86–989
See application file for complete search history.

(56) References Cited

U.S. PATENT DOCUMENTS

| | | | |
|---|---|---|---|
| 4,524,766 A | 6/1985 | Petersen | |
| 4,566,448 A | 1/1986 | Rohr, Jr. | |
| 4,718,413 A | 1/1988 | Johnson | |
| 4,722,330 A | 2/1988 | Russell et al. | |
| 4,759,350 A | 7/1988 | Dunn et al. | |
| 4,841,975 A | 6/1989 | Woolson | |
| 4,892,093 A | 1/1990 | Zarnowski et al. | |
| 4,935,023 A | 6/1990 | Whiteside et al. | |
| 5,002,547 A | 3/1991 | Poggie et al. | |
| 5,080,675 A | 1/1992 | Lawes et al. | |
| 5,122,144 A | 6/1992 | Bert et al. | |
| 5,219,362 A | 6/1993 | Tuke et al. | |
| 5,234,433 A | 8/1993 | Bert et al. | |
| 5,306,285 A | 4/1994 | Miller et al. | |
| 5,330,533 A | 7/1994 | Walker | |
| 5,342,366 A | 8/1994 | Whiteside et al. | |
| 5,413,579 A * | 5/1995 | Tom Du Toit | 606/87 |
| 5,417,694 A | 5/1995 | Marik et al. | |
| 5,417,695 A | 5/1995 | Axelson, Jr. | |
| 5,454,816 A | 10/1995 | Ashby | |
| 5,486,178 A | 1/1996 | Hodge | |
| 5,514,140 A | 5/1996 | Lackey | |

(Continued)

FOREIGN PATENT DOCUMENTS

FR           0337901       *   3/1989

OTHER PUBLICATIONS

International Preliminary Examination Report, May 10, 2005.

*Primary Examiner*—Pedro Philogene
(74) *Attorney, Agent, or Firm*—Baker & Daniels LLP

(57) ABSTRACT

A method and apparatus for performing total knee arthroplasty which is minimally invasive includes components with guide surfaces and slots for controlling the path of a cutting saw. The instrumentation permits resection of the proximal end of the tibia and distal end of the femur to be performed either medially or laterally with minimal cutting of soft tissue.

6 Claims, 12 Drawing Sheets

U.S. PATENT DOCUMENTS

| | | |
|---|---|---|
| 5,520,695 A | 5/1996 | Luckman |
| 5,562,675 A | 10/1996 | McNulty et al. |
| 5,569,261 A | 10/1996 | Marik et al. |
| 5,601,563 A | 2/1997 | Burke et al. |
| 5,609,639 A | 3/1997 | Walker |
| 5,624,444 A | 4/1997 | Wixon et al. |
| 5,658,292 A | 8/1997 | Axelson, Jr. |
| 5,662,656 A | 9/1997 | White |
| 5,683,397 A | 11/1997 | Vendrely et al. |
| 5,688,281 A | 11/1997 | Cripe et al. |
| 5,702,466 A | 12/1997 | Pappas et al. |
| 5,720,752 A | 2/1998 | Elliott et al. |
| 5,749,876 A | 5/1998 | Duvillier et al. |
| 5,782,920 A | 7/1998 | Colleran |
| 5,810,831 A | 9/1998 | D'Antonio |
| 5,830,216 A | 11/1998 | Insall et al. |
| 5,910,143 A | 6/1999 | Cripe et al. |
| 5,911,723 A | 6/1999 | Ashby et al. |
| 5,935,128 A * | 8/1999 | Carter et al. .................. 606/69 |
| 6,013,081 A | 1/2000 | Burkinshaw et al. |
| 6,059,831 A | 5/2000 | Braslow et al. |
| 6,102,954 A | 8/2000 | Albrektsson et al. |
| 2002/0198531 A1* | 12/2002 | Millard et al. ................ 606/87 |
| 2003/0212403 A1 | 11/2003 | Swanson |

* cited by examiner

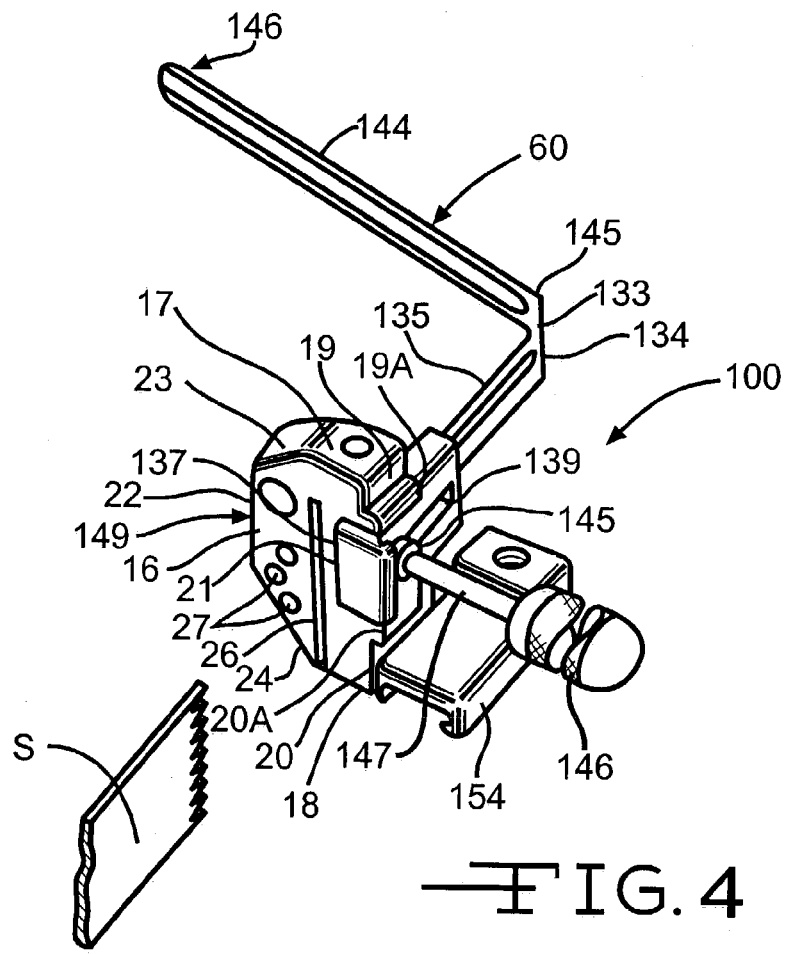
FIG. 4
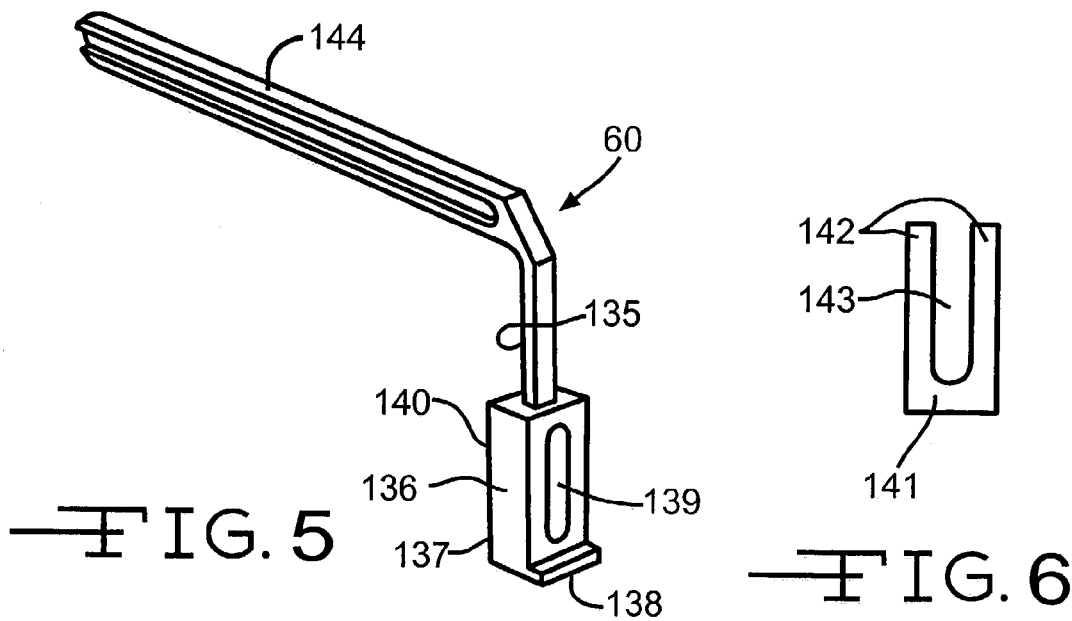
FIG. 5
FIG. 6

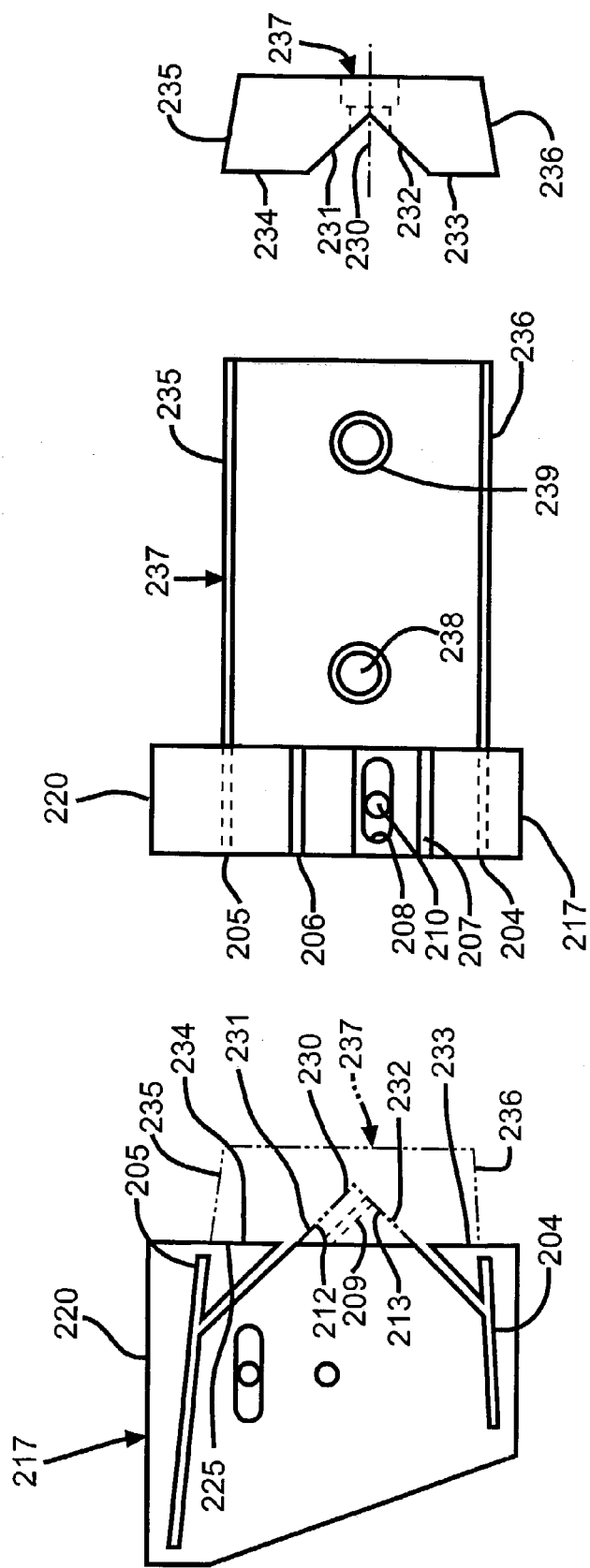

US 7,172,596 B2

MINIMALLY INVASIVE TOTAL KNEE ARTHROPLASTY METHOD AND INSTRUMENTATION

CROSS REFERENCE TO RELATED APPLICATION

This application is based upon and claims the benefit of U.S. Provisional Patent Application Ser. No. 60/361,990 filed Mar. 5, 2002.

BACKGROUND OF THE INVENTION

In performing knee surgery, it has long been an object to minimize the extent to which soft tissue is cut or otherwise damaged or disrupted. In the case of total knee arthroplasty (TKA), significant resectioning must be performed at the proximal end of the tibia and the distal end of the femur. Heretofore, the procedures involved in resecting the tibia and the femur necessitated significant cutting of soft tissue including muscles, tendons and ligaments. The instrumentation of the present invention and the methods utilized in performing total knee arthroplasty using such instruments significantly reduces the amount of cutting and other disruption and damage to such soft tissue with the result of faster recovery time for the patients.

Accordingly, it is an object of the present invention to provide new instrumentation for performing total knee arthroplasty with minimal cutting or other disruption of soft tissue such as muscles, tendons and ligaments.

It is another object of the present invention to provide a method for performing total knee arthroplasty using such instrumentation.

SUMMARY OF THE INVENTION

The instrumentation of the present invention includes a number of interacting components with guide surfaces and slots for controlling the path of a cutting saw, with alignment means for properly positioning the guide surfaces and with protective elements for moving specific items of soft tissue such as ligaments away from the path of the cutting saw during the step of resecting in that area or blocking the movement of such saw beyond a specified point in the resecting process. A significant feature of the present invention is the design embodiments which permit resection of both the proximal end of the tibia and distal end of the femur to be performed either medially or laterally as contrasted with prior art resectioning performed anteriorly.

In the varus knee, a curvilinear medial incision is made from the superior pole of the patella to the tibial joint line. The arthrotomy is in line with the skin incision. A transverse incision can be made about 2 centimeters beneath the vastus medial to facilitate the exposure. The extension becomes less necessary with additional experience with the operative approach. In the valgus knee, a vertical incision may be made on the lateral side of the patella extending distally to the tibial joint line. The arthrotomy is performed in a vertical fashion and the iliotibial band is pealed from the tibial plateau joint line from anterior to posterior. It is preferred to use the medial approach for all knees but the lateral incision may be used.

BRIEF DESCRIPTION OF THE DRAWINGS

FIG. 4 is a perspective view showing a femoral cutting guide assembly including an intramedullary guide for controlling the positioning of the femoral cutting guide.

FIG. 5 is a perspective view of the intramedullary guide portion of the assembly shown in FIG. 4.

FIG. 6 is a plan view of a wedge for use, where necessary, in making adjustments to the depth of cutting using the instrumentation shown in FIG. 4.

FIG. 12A is an enlargement of that portion of the sizer guide within the circle identified as "See FIG. 12A" shown in FIG. 12.

FIG. 17 is a view similar to FIG. 15 but showing in dashed lines an anterior/posterior femoral resection block used in combination with the anterior/posterior femoral resection guide.

FIG. 18 is a front view of the anterior/posterior femoral resection block of FIG. 17 in combination with the anterior/posterior resection guide.

FIG. 19 is a side view of the anterior/posterior resection block per se.

DETAILED DESCRIPTION OF THE INVENTION

Figure 1:
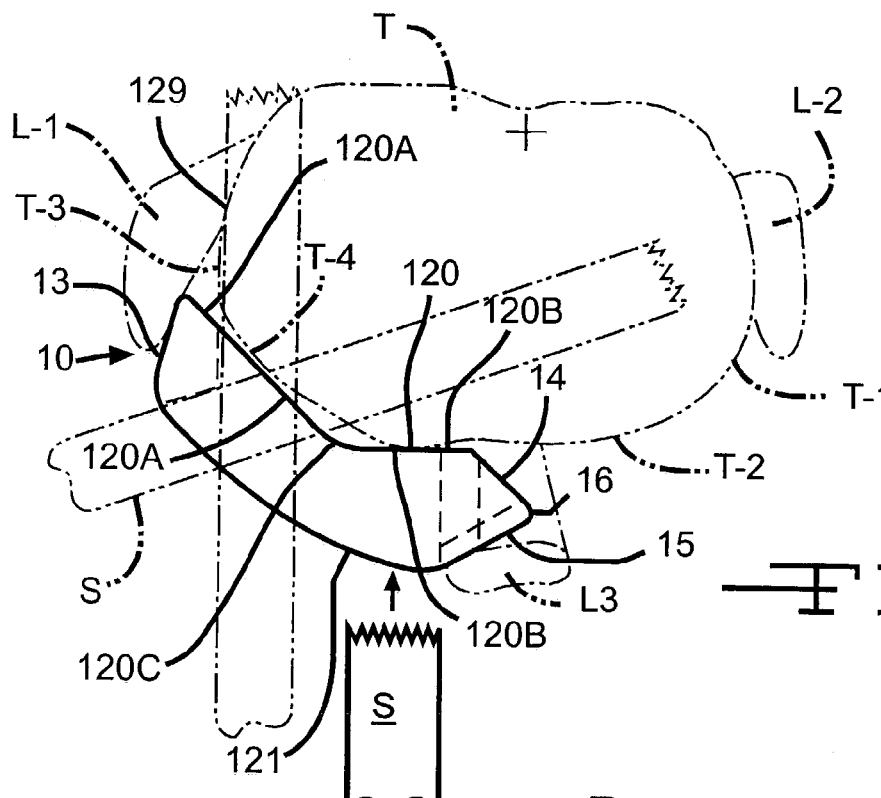
FIG. 1 is a plan view of a tibial resection guide showing cutting of the proximal end of the tibia cutting from the medial side.
Figure 2:
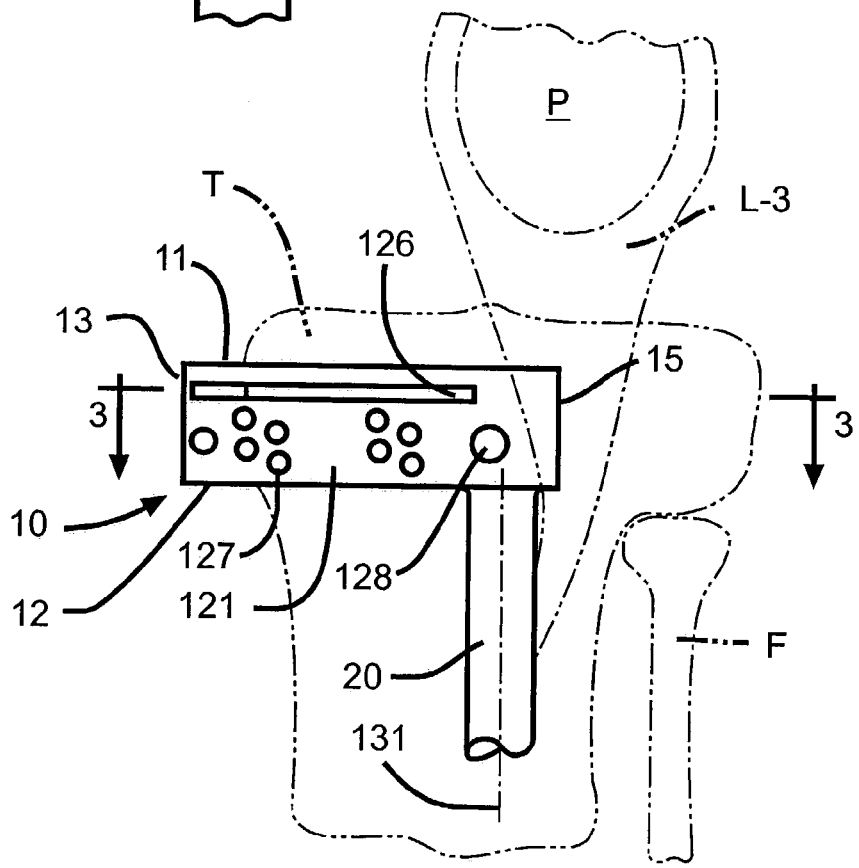
FIG. 2 is an elevational view of the tibial resection guide of FIG. 1 showing it positioned at the proximal end of the tibia being resectioned.
Figure 3:
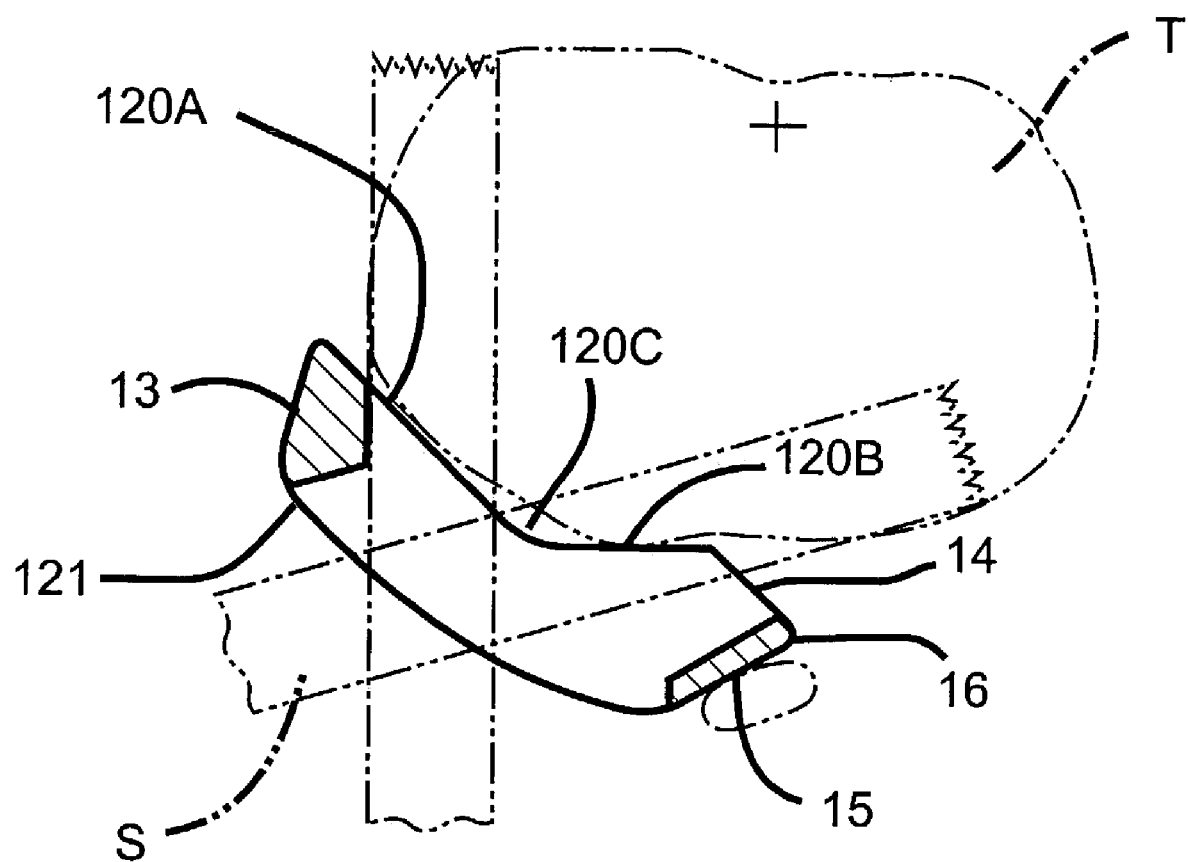
FIG. 3 is a sectional view taken through line 3—3 of FIG. 2.
Figure 7:
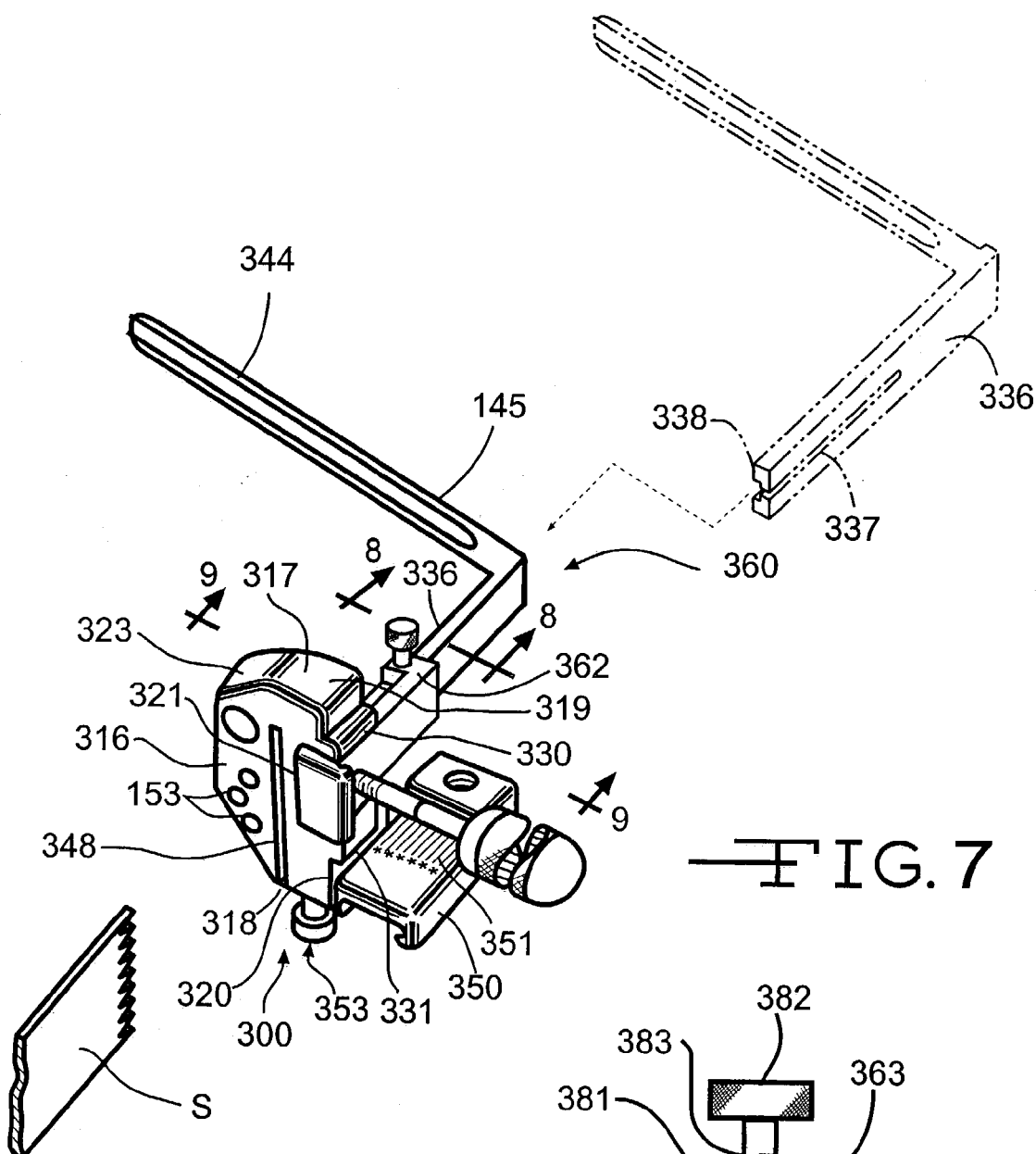
FIG. 7 is a view similar to FIG. 4 showing a modified embodiment of femoral cutting guide.
Figure 8:
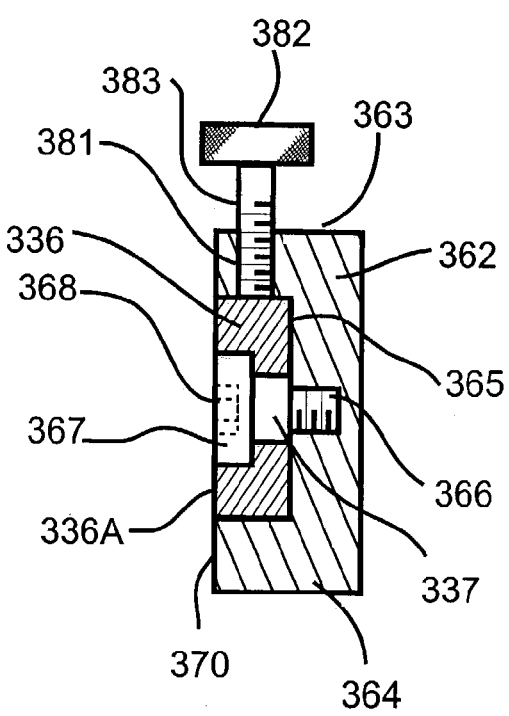
FIG. 8 is a sectional view taken through line 8—8 of FIG. 7.
Figure 9:
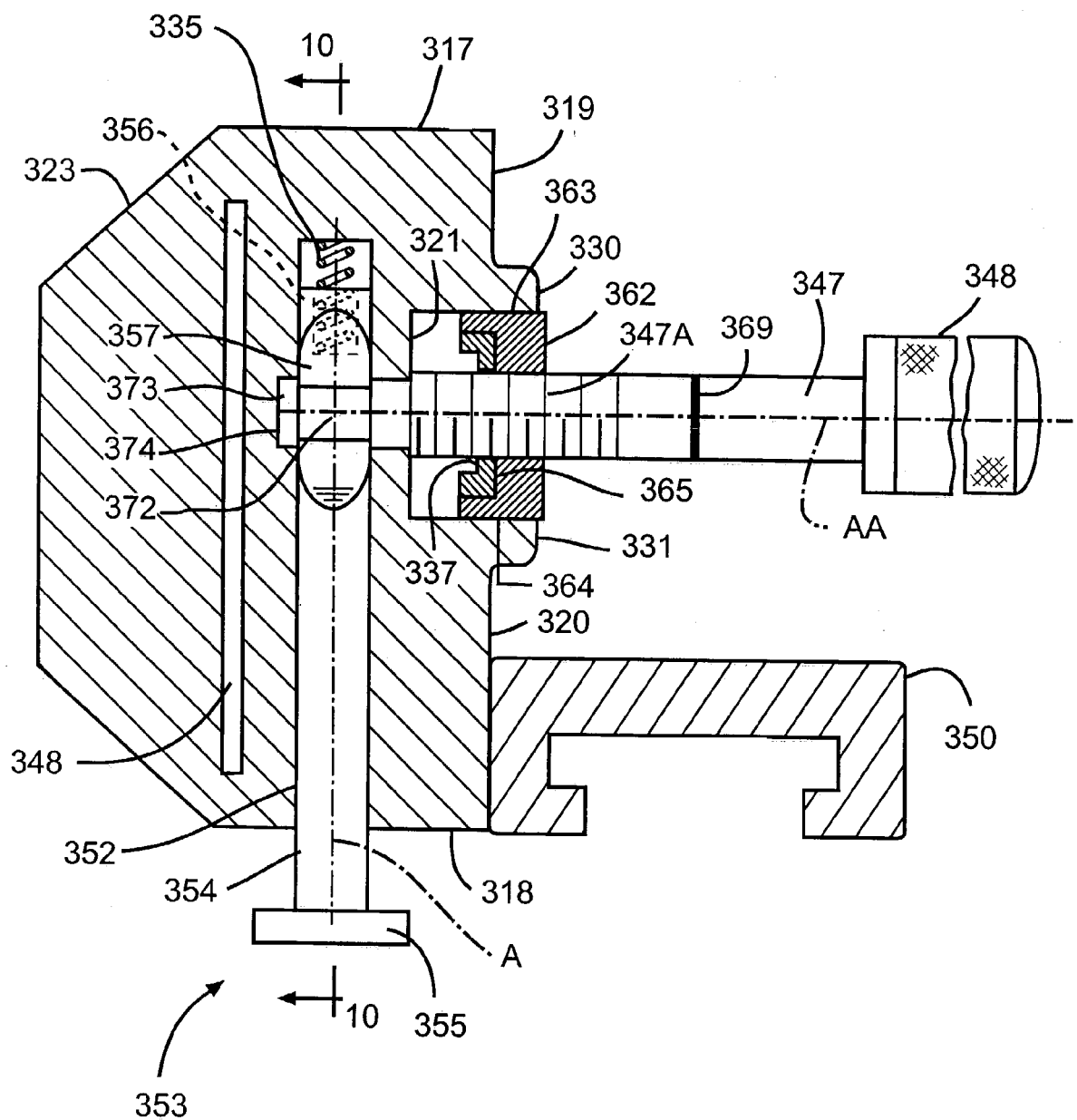
FIG. 9 is a sectional view taken through line 9—9 of FIG. 7.

Referring to FIGS. 1–3, there is shown a tibial resection guide generally designated by the number 10 and shown positioned in use at the proximal end of a tibia T shown in dashed lines. For point of reference, the tibia T is shown with areas designated as follows: lateral cortex T1, anterior cortex T2, medial cortex T3, and anterior medial cortex T4. Also shown in dashed lines in FIG. 1 is a medial collateral ligament L-1, a lateral collateral ligament L-2 and patella tendon L-3 attached to patella P. The fibula F and patella P is shown in dashed lines in FIG. 2 along with the patella tendon L-3.

The tibial resection guide 10 has a flat proximal surface 11 (upper surface as viewed in FIG. 2) intended for positioning in the area of the proximal end of the tibia T and a flat lower surface 12 distally thereof when properly position for resecting the tibia T. The tibial resection guide 10 has a tibia engagement wall 120 extending between the proximal surface 11 and lower surface 12. The engagement wall is contoured to engage and somewhat wrap around the surface of the tibia in the area of the medial cortex T3 and anterior medial cortex T4 and extends to a central portion of the anterior side of tibia T. As shown in FIG. 1, the engagement wall includes a first planar section 120A, a second planar section 120B and a curved section 120C between the first and second planar sections 120A and 120B. The tibial resection guide 10 also has an opposing wall 121 spaced from the wall 120.

An end wall 13 extends between a first planar section 120A of the engagement wall 120 and the opposing wall 121 at the end intended to be positioned adjacent the medial cortex T-3. The portion of the tibial resection guide 10 in the area of the juncture between the end wall 13 and the engagement wall first planar section 120A defines surfaces tapering toward one another and positioned to fit under the medial collateral ligament L-1 to displace it or otherwise protect it from damage by the saw during resectioning. At the opposite end of the tibial resection guide 10, the engagement wall second planar section 120B extends to a line of juncture with a first tapered wall 14 which flares outwardly away from the tibia T to which the tibial resection guide 10 is engaged. A second tapered wall 15 extends toward the tibia T from the end of the opposing wall 121 and joins the first tapered wall at an apex 16. The portion of the resection guide 10 in the area of the first and second tapered walls 14 and 15 and the apex 16 are positioned to displace or otherwise protect the patella tendon L-3 from damage by the saw during resectioning. A slot 126 for receiving a saw blade S extends between the opposing wall 121 and the tibia engagement wall 120. As may be seen in FIGS. 1 and 3, the saw S may be positioned to cut from the lateral aspect to the medial aspect.

The tibial resection guide 10 has a plurality of holes 127 and 128 which extend between the engagement surface 120 and the opposing surface 121. A combination alignment guide and support member 20 extends from the lower surface 12 along an axis 131 which is perpendicular to the slot 126.

In preparation for performing resectioning of the tibia T, the tibial resection guide 10 is positioned with the slot 126 at the desired location adjacent the proximal end of the tibia T with the guide/support member 29 positioned such that its axis 131 is parallel to the mechanical axis of the tibia T so that the slot 126 guiding the cutting saw S is perpendicular to the mechanical axis of the tibia T. This alignment is important in order to insure that the cut, when made using the slot 126 as a guide, is not in a varus or valgus misalignment and to determine correct degree of posterior slope of the cut or resection of the tibial plateau. The distal end of the guide/support member 20 may be attached to the ankle area by means well known in the art to insure alignment parallel to the mechanical axis of the tibia T. Holding pins may then be inserted through selected ones of the holes 127 and 128 as determined by the surgeon and attached to the tibia T to retain the resection guide 10 in position as is well known in the art.

In moving the resection guide 10 into the properly aligned position, the surgeon carefully manipulates the resection guide 10 to displace the medial collateral ligament L-1 with that portion of the resection guide 10 in the area of the juncture between end wall 13 and engagement wall first planar section 120A and to displace the patella tendon L-3 with that portion of the resection guide 10 adjacent the apex 16. With the ligament L-1 and patella tendon L-3 thus displaced, a saw S may then be position in the slot 126 to cut the proximal end from the tibia T without cutting either of the medial collateral ligaments L-1 or the patella tendon L-3.

The foregoing description of the tibial resection guide is for a guide intended for use in performing surgery on the medial side of a left knee or the lateral side of a right knee. A similar tibial resection guide with the areas repositioned in obvious fashion may be used in performing surgery on the lateral side of the left knee or the medial side of the right knee is within the scope of the present invention.

FIGS. 4–26 are directed to cutting guide embodiments for use in resectioning the distal end of a femur.

In resectioning the distal end of a femur, it is important that the condyles be cut such that the resected distal surface facing the tibia is perpendicular to the mechanical axis of the patient's femur. A common procedure in prior art total knee arthroplasty involves drilling a hole in the intramedullary canal several inches along the anatomical axis of the femur starting slightly anterior to the intercondylar notch. The anatomical axis extending from the sulcus at the center of the femur between the condyles to the center of the femoral trochanter is at a slight angle, usually 5 to 6 degrees, to the mechanical axis which extends from the center of the femoral head through the sulcus to the center of the ankle. Following drilling, an alignment rod is positioned in the hole along the intramedullary canal and extends outwardly therefrom. An alignment guide used in combination with the alignment rod directs the cutting instrument along the proper path, anterior to posterior, of the condyles to be cut.

U.S. patent application Ser. No. 09/973,584 filed Oct. 9, 2001, which includes common inventors with the inventors hereof, discloses a femoral knee saw guide which uses extramedullary means to provide proper alignment for guiding a saw or other cutting instrument along the proper path for resectioning the distal end of the femur while permitting the cutting to be performed in a lateral to medial direction or medial to lateral direction. The distal femoral guide assembly of the embodiments of FIGS. 4–26 also permit the resectioning to be performed in a lateral to medial direction or medial to lateral direction but does so using an intramedullary arm as part of the assembly for obtaining proper alignment. Adjustment means are also provided for readily varying the depth of the cut.

Referring to FIGS. 4–6, there is shown an intramedullary knee distal femoral cutting guide assembly 100 which includes a cutting guide 149, a plate 154 welded thereto and an intramedullary arm assembly 60.

The cutting guide 149 has a trapezoidal shape when viewed from the front side 16 or the backside which is parallel thereto. It extends lengthwise from a first end 17 to a second end 18. Adjoining the first end 17 and perpendicular thereto is a first planar wall section 19 extending toward the second end 18. Extending from the second end 18 toward the first end 17 is a second planar wall section 20 which is perpendicular to the second end 18 and lying in the same plane as the first planar wall section 19. Extending outwardly from the first planar wall section 19 is a first enlarged shoulder 19A. Extending outwardly from the second planar wall section 20 is a second enlarged shoulder 20A. An elongated recess 21 separates the first enlarged shoulder 19A from the second enlarged shoulder 20A. Positioned in and extending outwardly from the recess 21 is an intramedullary arm assembly 60, the function of which will be hereinafter described.

Spaced from and parallel to the first and second planar wall sections 19 and 20, is a lateral wall section 22. Extending between the lateral wall section 22 and the first end 17 is a first tapered wall 23 which is disposed at an angle on the order of 50° relative to the plane defined by the lateral wall section 22. Extending from the lateral wall section 22 to the second end 18 is a second tapered wall 24 which is disposed at an angle on the order of 32° relative to the plane defined by the lateral wall section 22.

Extending through the cutting guide 149 is an elongated guide slot 26 spaced substantially midway between and parallel to (i) the first and second wall sections 19, 20 and (ii) to the lateral wall section 22. The slot 26 extends completely through the cutting guide 149 from the front 16 to the back and extends approximately 80% of the distance between the first end 17 and second end 18, with one end of the slot 26 being only slightly spaced from the second end 18 and the opposite end being spaced a greater distance from the first end 17. Extending completely through the cutting guide 149 from the front 16 to the back are a plurality of three holes 27 which extend along axes which are substantially perpendicular to the front 16 and positioned in the space between the lateral wall section 22 and the slot 26. The holes 27 receive pins with which the surgeon may fasten the cutting guide 149 to the lateral or medial aspect of the femur undergoing the surgical procedure.

As mentioned previously, the anatomical axis of a patient's femur is at a slight angle relative to the mechanical axis. Although such angle is usually in the range of 5 to 6° it can vary between 2° and 8° and, in extreme cases, possibly more. The distal femoral cutting guide assembly 100 with its cutting guide 149, arm assembly 60 and related members are designed to assist the surgeon in obtaining a cut which is perpendicular to the mechanical axis while permitting the cutting to be performed from lateral to medial or medial to lateral directions. Also disclosed are means for readily adjusting the depth of cut to be made. The surgeon can determine for any given patient the approximate angle between such patient's anatomical axis and mechanical axis and the desired depth of cut.

The arm assembly 60 includes an alignment member 144 sized to be positioned in a predrilled hole drilled into the medullary canal through the intercondylar notch along the anatomic axis of the femur. A stylus arm 135, which preferably is formed as an integral unitary part of the alignment member 144, is disposed at an angle relative to the longitudinal axis of the alignment member 144 and has supported on the end thereof a stylus 137 having an elongated slot 139 extending therethrough which is substantially parallel to the stylus arm 135. The stylus 137 is sized to be slideably positioned in the recess 21 of the cutting guide 149. The stylus 137 has a smooth rear surface 140 which is slideably engaged with the alignment member 149 and a front surface from which extends a flange 138 for gripping by the surgeon.

A locking handle 146 has a stem 147 extending therefrom. The stem 147 has a threaded end (not shown) engaged to a threaded hole (not shown) formed in the cutting guide 149 at the bottom of the recess 21. The stem 147 has an enlarged shoulder 145 which engages the outer surface of the stylus 137 on opposite sides of the slot 139 when the threaded end of the stem 147 is tightly engaged to the cutting guide. Prior to tightening the locking handle 146 and threaded stem 147, the cutting guide 149 may be moved as necessary to engage the medial or lateral side of the femur being resectioned when the alignment member 144 is positioned in the prepared intramedullary channel of the femur. Such movement of the cutting guide 149 will move the recess 21 relative to the stylus 137.

As previously discussed, it is desirable to make the resection cut substantially perpendicular to the mechanical axis of the patient's femur. The positioning of the alignment member 144 in the prepared intramedullary channel positions it along the anatomical axis of the femur. In order to obtain positioning of the cutting guide 149 such that a cut made with a saw S extending through the slot 26 is perpendicular to the mechanical axis, the surgeon selects an intramedullary arm assembly 60 which has the appropriate angle between the alignment member 144 and the stylus arm 135 for the femur being resected. For example, an intramedullary arm assembly 60 in which the angle between the alignment member 144 and the stylus arm 135 may selected as being 94° for a patient whose anatomical axis is at an angle of 4° to the mechanical axis, or 96° for a patient where such angle is 6°, or 98° for a patient where such angle is 8° and more or less in similar fashion for patients whose mechanical axis vary from the anatomical axis by other amounts. These angles are valid for the medial approach. The reverse is true for the lateral approach. The lateral angles decrease, requiring different alignment arms for the lateral approach. For example, for a patient whose anatomical axis relative to the mechanical axis is noted as follows, the angle between the alignment member 144 and the stylus 135 will be as follows for the lateral approach:

| Patient Angle | Alignment member/stylus angle |
| --- | --- |
| 4° | 86° |
| 6° | 84° |
| 8° | 82° |

In use, the surgeon selects an intramedullary arm assembly 60 having the proper angular displacement between the alignment member 144 and the stylus arm 135 for that particular patient. Following drilling of a hole in the intramedullary canal and positioning the alignment member 144 therein to a position at which the stylus arm 135 engages the distal end of the patient's condyles, the cutting guide 149 may be adjusted by moving it toward the alignment member 144 with the stem 147 moving through the slot 139 of the stylus 137 until the cutting guide 149 engages the lateral or medial aspect of the patient's femur to be resected. The amount of condyles which will be removed by a cutting saw S using the slot 26 to guide it will be equal to the distance from the cutting surface of the saw S to the surface of stylus arm 135 engaged to the end of the condyles.

Upon engagement of the cutting guide 149 against the patient's femur, the locking handle 146 and threaded stem 147 are rotated to tightly engage the shoulder 145 against the stylus 137. Prior to performing the cutting operation, it is desirable to secure the cutting guide 149 to the femur following its proper alignment by means of pins positioned through the holes 27.

Referring to FIG. 6, there is shown a wedge 141 having a pair of arms 142 separated by a slot 143. The wedge may have a thickness on the order of 2 mm or other desired thickness as determined by the surgeon. If the surgeon determines that it is necessary to cut more of the distal end of the femur, he simply positions a wedge 141 having a thickness equal to the desired amount of additional bone to be removed between the rear surface 140 of the stylus 137 and the recess 21 of the cutting guide 149. This has the effect of moving the cutting slot 26 proximally from the distal end of the femur the same distance as the thickness of the wedge.

Referring to FIGS. 7–11, there is shown a modified distal femoral cutting guide assembly 300 which permits adjustment of the depth of cutting of the distal end of the femur without the necessity of using a wedge such as the wedge 141 of FIG. 6 in the embodiment previously discussed. The modified embodiment of distal femoral cutting guide 300 includes a cutting guide block 323 which is similar to the cutting guide block 149 of the embodiment of FIG. 4 in that it includes a front surface 316, a first end 317, a second end 318, a cutting slot 348 and first and second planar wall sections 319 and 320. The cutting guide block 323 are also encloses a first enlarged flange 330 extending outwardly from the first planar wall surface 319 and a second enlarged flange 331 extending outwardly from the second planar wall section 320. The first and second enlarged flanges 330 and 331 cooperate with a rear wall to define a recess 321 for receiving a modified intramedullary arm assembly 360. Welded to the cutting guide block at the second planar wall section 320 is a base member 350 having a series of lines 351 forming a scale including numbers for ascertaining the depth of the cut which will be made by a saw S guided through the cutting slot 348.

Extending inwardly from the second end 318 along an axis A is a longitudinal passageway 352 (see FIGS. 9–11) in which is positioned a plunger 353 having a stem 354 with a cylindrical or, preferably rectangular cross section and an enlarged head 355. The plunger stem 354 has a cavity 356 at the end opposite the enlarged head 355 in which is positioned a compression spring 335 urging the plunger 353 outwardly toward the position shown in FIGS. 9 and 10. The plunger stem 354 has a recess 357 extending inwardly toward the longitudinal axis of the stem in an area near the bottom of the cavity 356.

The intramedullary arm assembly 360 includes an intramedullary alignment member 344 intended for positioning in the intramedullary canal of the femur following drilling thereof. A stylus arm 336, which is preferably an integral unitary part of the intramedullary arm assembly 360, extends from the end of the intramedullary alignment member 344 at an angle in the range of 94° to 98°, more or less depending upon the patient. As can be seen in phantom lines in FIG. 7, the stylus arm 336 is provided with a longitudinally extending slot 337 extending inwardly from its end 338 toward the juncture of it with the intramedullary alignment member 344.

Figure 10:
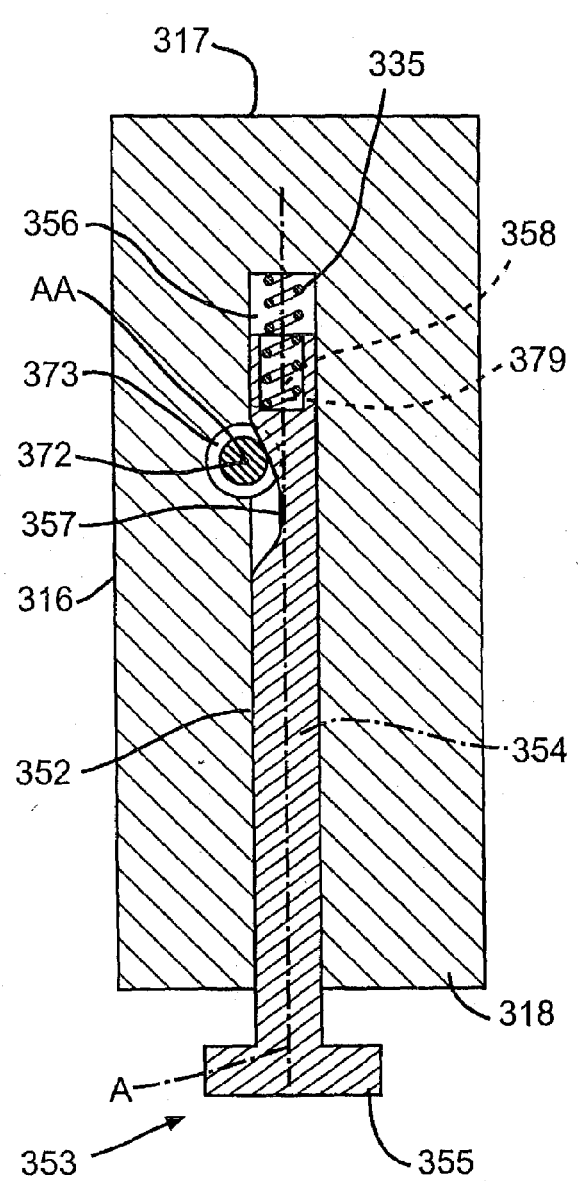
FIG. 10 is a sectional view taken through line 10—10 of FIG. 9.
Figure 11:
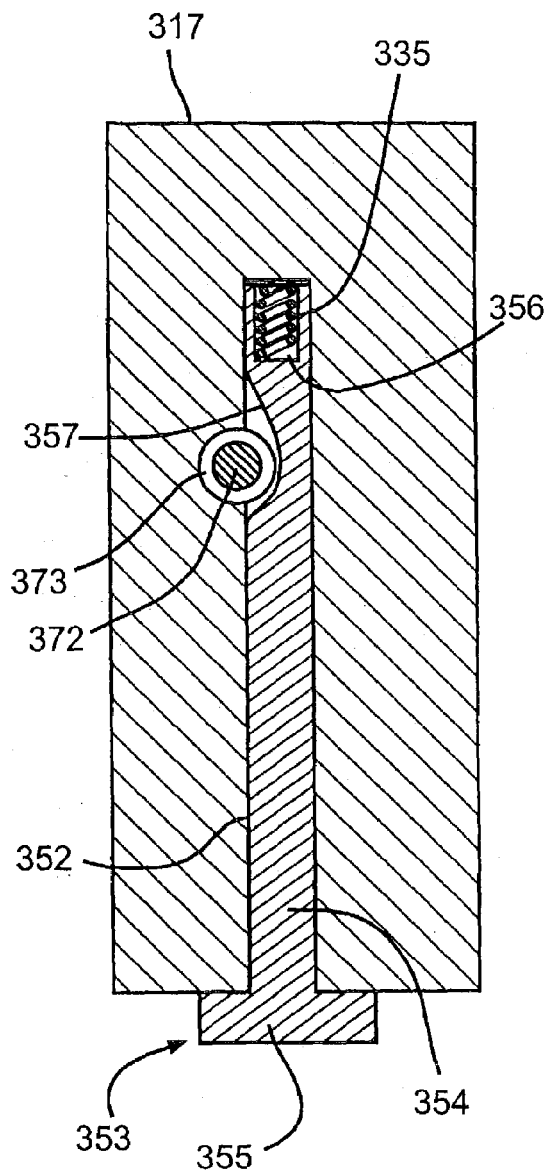
FIG. 11 is a view similar to FIG. 10 but showing the plunger fully depressed.

The stylus arm 336 is slideably received in a housing 362. The housing 362 is received in the recess 321 for slideable movement inwardly or outwardly therein and has an upper edge 363 engaged to the lower surface of the first enlarged flange 330 and a lower surface 364 engaged to the upper surface of the second enlarged flange 331. The housing 362 has a channel shaped recess 365 in which that portion of the stylus arm 336 in the area of the slot 337 is positioned. The stylus arm 336 is retained in the channel shaped recess 365 by means of a threaded nut 366 (see FIG. 8) having an enlarged head 367 and an alien wrench cavity 368 engaged in a threaded cavity of the housing 362. The threaded nut 366 is only loosely engaged to the stylus arm 336 in order to permit the stylus arm 336 to slide within the channel shaped recess 365 of the housing 362. Threadedly engaged to the housing 362 is a rotatable handle assembly having a gripping handle 348 and a stem 347 with outwardly facing threads 347A engaged to threads of the housing 362. The stem 347 extends along an axis AA and includes an area 372 of reduced size beyond the threads 347A and terminates in an enlarged head 373 positioned in a cavity 374 in the cutting guide block 323. The longitudinal axis of AA of the stem 347 is slightly offset from the axis A of the passageway 352 in which the plunger stem 354 is positioned to an extent that the area of reduced size 372 of the threaded stem 347 extends partially into the longitudinal passageway 352. The depth to which the recess 357 of the plunger stem 354 extends inwardly toward the axis A is such that when the plunger 353 is in its fully depressed position shown in FIG. 11 against the urging action of compression spring 335, the area of maximum depth of such recess will be aligned with the reduced sized portion 372 of the threaded stem 347. The size and depth of such recess 357 is such as related to the size of the enlarged head 373 retained in the recess 374 as to permit withdrawal of the threaded stem 347 including the enlarged head 373 during disassembly from the cutting guide block 323 or movement inwardly beyond the plunger 354 during assembly. When in the assembled position for use in resecting the distal end of the femur, the plunger 355 will remain in its extended position shown in FIG. 10. When in such extended position, a portion of the surface of the enlarged head 373 adjacent the reduced sized portion 372 will engage the plunger 355 as shown in FIG. 10 (see dotted line 379) to hold the stem 347 in a fixed position relative to the cutting guide block 323. As a result, rotation of the threaded stem 347 within the threaded passageway of the housing 362 will cause the cutting guide block 323 and its cutting guide slot 348 to move inwardly or outwardly relative to the housing 362 and the stylus arm 336 supported therein. Such relative movement will result in adjusting the depth to which the distal end of the femur will be cut.

The stem 347 is provided with a calibrated mark 369 which may be observed with the lines 351 of base member 350 in order to ascertain the depth of cutting which is the distance from the cutting slot 348 to the surface of the stylus arm 336 engaged to the distal end of the femur.

Following the placement of the intramedullary guide 344 in the drilled medullary canal of the femur, it is necessary to slide the cutting guide block 323 into engagement with the lateral or medial aspect of the femur. In order to accomplish this, the housing 362 in which the end 338 and adjacent portion of the stylus arm 336 is positioned is provided with a threaded aperture 381 overlying the stylus arm 336. An adjustment knob 382 having a threaded stem 383 is threadedly engaged to the threaded aperture 381 and upon tightening thereof places the stylus arm 336 in a fixed position relative to the housing 362. Upon loosening the knob 382 and the threaded stem 383, the cutting guide block 323 may be readily moved relative to the stylus arm 336 and intramedullar guide 344 to reach the medial or lateral aspect of the femur.

When the housing 362 is positioned in the recess 321 of the cutting guide block 323, the outwardly facing surface 336A of the stylus arm and a rear surface 370 of the housing 362 can be moved from an inward position engaged to the rear surface of the recess 321 to an outward position spaced from such rear surface (see FIG. 9) by rotating the threaded stem 347 in the housing 362. As can be seen from FIG. 9, since the stem 347 is in a fixed position relating to the housing 362, only the stylus arm 336 is slideable longitudinally in the recess 321.

Figure 12:
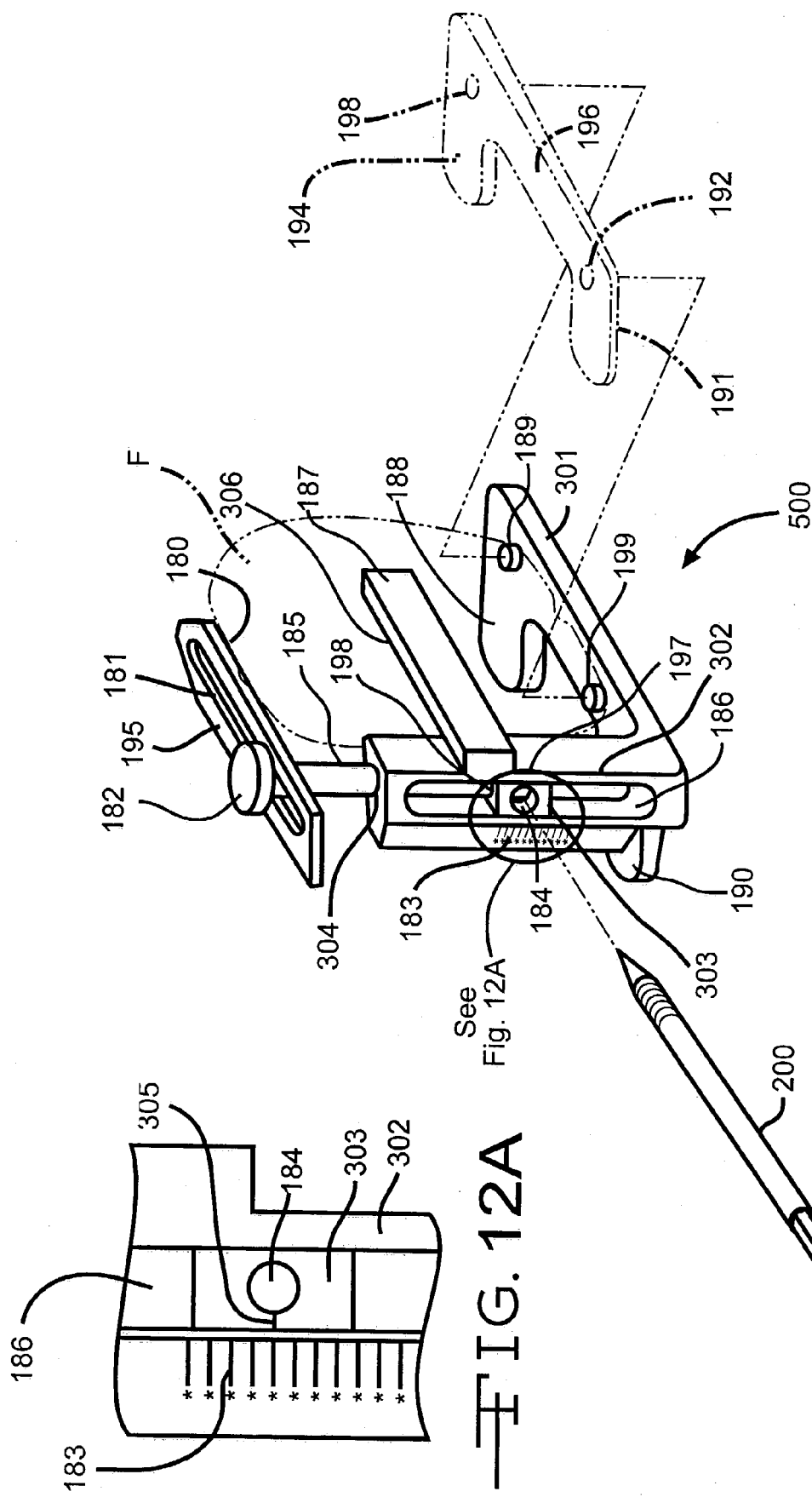
FIG. 12 is a perspective view of a femoral anterior/posterior side loading sizer guide.
Figure 13:
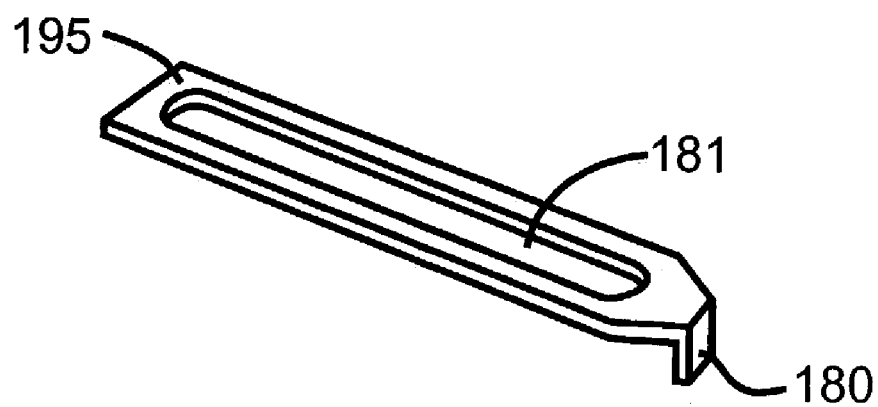
FIG. 13 is a perspective view of a stylus intended for use with a femoral interior/posterior side loading sizer guide of the type shown in FIG. 12.
Figure 14:
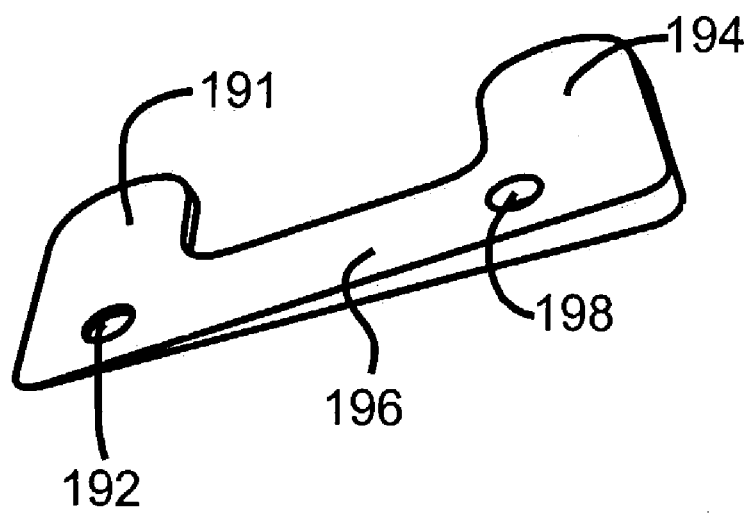
FIG. 14 is a perspective view of a posterior wedge intended for use with the sizer guide of FIG. 13.

Referring to FIGS. 12–14, there is shown a femoral anterior-posterior side loading sizer guide generally designated by the numeral 500. The sizer guide 500 has a dual function in that (1) it sizes the femur to assist in obtaining the proper size for the prosthesis and selection of appropriate cutting blocks and (2) it sets the external rotation for the prosthesis being implanted to assure proper patella tracking. The setting includes the step of positioning a guide pin for use with an anterior-posterior femoral resection guide to be hereinafter described with reference to FIGS. 15–22. The sizer guide 500 is side specific in that there is a unit for the right medial-left lateral knee resection and a separate unit for the left medial-right lateral knee resection.

The sizer guide 500 includes a base 301 having a central portion with a first foot 188 at one end and a second foot 190 at the opposing end and cooperating with the central portion to define a U-shaped structure. Extending upwardly from the end of the base 301 in the area of the second foot 190 is an upstanding support member 302 which, preferably, is integral and unitary with the base 301 and disposed substantially at right angles thereto. The upstanding support member 302 has an elongated slot 186 extending through a major portion thereof. Positioned in the slot 186 is a slideable guide member 303 mounted on the end of a plunger rod 185 which extends through an aperture 304 in the upper end of the upstanding support member 302. The plunger rod 185 is snuggly received in the aperture 304 for slideable movement therein. If desired, the plunger 185 and the aperture 304 could be threaded for a rotatable adjustment means to raise or lower the slideable guide member 303. In that case, the plunger rod 185 would be rotatable relative to the guide member 303. The upper end of the plunger rod 185 has an enlarged nut 182 for gripping and moving the plunger rod 185 and the slideable guide member 303 upwardly or downwardly in the slot 186.

The slideable guide member 303 is slideable in the slot 186 but in close relationship therewith so that the walls of the slot 186 prevent rotational movement of the slideable guide member 303. Extending through the slideable guide member 303 along an axis parallel to the base 301 is a guide alignment hole 184. In an area of the upstanding support member 302 adjacent the slot 186 is a calibrated scale 183. Extending radially outwardly from the guide alignment hole 184 is a mark 305 etched or otherwise formed in the slideable guide member 303 which upon alignment with a specific mark on the scale 183 will provide the surgeon with the anterior-posterior dimension of the distal end of the femur F.

An anterior femoral stylus 195 having an elongated slot 181 is affixed to the plunger rod 185 immediately below the flat-headed nut 182. The anterior femoral stylus 195 rests on a shoulder at the upper end of the plunger rod 181 and may be firmly engaged thereto upon tightening of the flat-headed nut 182. Upon loosening of the flat-headed nut 182, the anterior femoral stylus 195 may be adjusted inwardly or outwardly and rotationally to engage the desired anterior area of the femur F.

Rigidly secured to the upstanding support member 302 on the opposite side of the slot 186 from the scale 183 is a distal condylar arm 187. The distal condylar arm 187 is substantially parallel to the base 301 and has a flat engagement surface 306 intended to engage the resected surface of the distal end of a femur F shown in dashed lines in FIG. 12.

Extending upwardly from the base are a pair of upstanding pegs 189 and 199. Also provided for engagement with the base 301, if needed depending upon the degree needed to properly set the external rotation of the cuts for the specific knee involved, is a wedge 196 extending from a first end 191 to a second end 194 and having a first aperture 192 and a second aperture 198 which are sized to be snuggly engaged by the pegs 199 and 189, respectively. The wedge 196 is tapered from a relatively thin thickness adjacent the first end 191 to a greater thickness adjacent the second end 194. The surgeon may select a wedge 196, if one is needed, from a series of wedges having a degree of taper between the upper and lower surfaces, from first end 191 to second end 194 varying between 1° to 8°. The purpose of the wedge 196 is to obtain proper angular alignment depending upon the anatomical structure of the femur involved in the surgery.

In use, the anterior-posterior side loading sizer guide 500 is positioned with the foot members 188 and 190 contacting the posterior femoral condyles when in flexion. In those situations in which a wedge 196 is required for use, the posterior femoral condyles will be engaged by the respective portions of the wedge 196 overlying the feet 188 and 190. The sizer guide 500 is then positioned with the distal condylar arm 187 against the resected distal femur F. Thereafter, the plunger 185 carrying the anterior femoral stylus 195 is lowered to contact the anterior femur F. Such positioning permits the surgeon to check the alignment of the mark 305 on the scale 183 to determine the anterior to posterior dimension of the femur F. Following such positioning, a guide pin 200 is inserted through the guide alignment hole 184 and drilled into the femur F. The drilling using the alignment hole 184 as a guide causes the guide pin 200 to be directed in the correct angular rotational position, for example, 3°, 5° or 7°. The guide pin 200 is left in position following removal of the sizer guide 500 from the femur F. The guide pin 200 is then in position to assist in aligning the anterior/posterior femoral resection guide to be described with respect to FIGS. 15–22.

Figure 16:
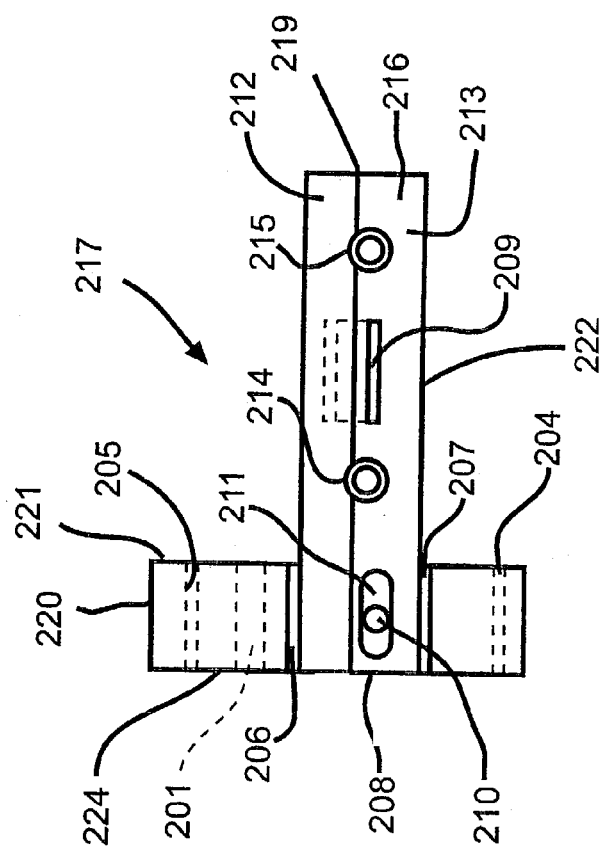
FIG. 16 is a front view of the anterior/posterior chamfer femoral resection guide of FIG. 15.
Figure 15:
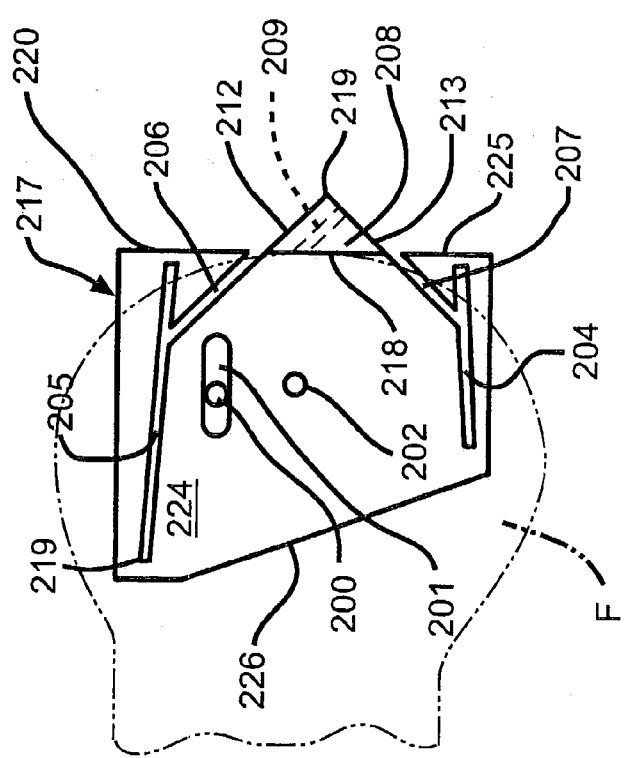
FIG. 15 is a side view of an anterior/posterior chamfer femoral resection guide.

Referring now to FIGS. 15 and 16, there is shown a side femur resection guide generally designated by the numeral 217 including a side chamfer block 220 having a flat knee engagement surface 221 (FIG. 16) intended to engage either the medial side of the right knee or lateral side of the left knee in which the headless guide pin 200 of FIG. 12 has been positioned. An outer surface 224 is parallel to the engagement surface 221. An elongated slot 201 for receiving the guide pin 200 extends through the side chamfer block 220 from the outer surface 224 through the engagement surface 221.

The side chamfer block 220 has a distal edge 225 which will be aligned with the prepared distal end of the femur F and an opposed proximal edge 226.

Attached to the distal edge 225 and extending from the side chamfer block 220 at substantially right angles to the flat surface 221 is a distal end chamfer block 222 having a first chamfer surface 212 and a second chamfer surface 213 disposed at right angles to one another and meeting at an apex 219. The distal end chamfer block 222 extends outwardly from the flat surface 221 of the side chamfer block 220 and has a triangular cross-sectional configuration defined by the first and second chamfer surfaces 212 and 213 and by a third surface 218 which is flat and engages the distal edge 225 and the prepared distal end of the femur F. The distal end chamfer block 222 has a slot 211 and is secured to the side chamfer block 220 by means of a pin 210 extending through the slot 211 and into distal edge 225. The distal end chamfer block 222 may be adjusted medially to laterally or laterally to medially prior to tightening the pin 210. Extending through the distal end chamfer block 222 from the second chamfer surface 213 to the third surface 218, along a path substantially parallel to the first chamfer surface 212, is a central guide slot 209 for cutting a portion of a notch in the resected distal end of the femur F to accommodate a retention notch on a prosthesis to be implanted thereon. With the ability to move the distal end chamfer block 222 laterally to medially as a result of the presence of the slot 211, the central guide slot 209 may be properly positioned for accurate cutting of one portion of the notch. The distal end chamfer block 222 is also provided with a pair of apertures 214 and 215 for receiving pins or screws to secure the distal end chamfer block 222 to the resected distal end of the femur. The apertures 214 and 215 are provided with internal threads.

The side chamfer block 220 is provided with a posterior cutting slot 204 for directing and guiding a cutting saw near the posterior of the femur distal end and an anterior cutting slot 205 for guiding the movement of a cutting saw near the anterior of the distal end of the femur F. Cutting with a saw using the cutting slots 204 and 205 as a guide is performed medially to laterally or laterally to medially. An angled guide slot 206, one surface of which is co-planar with a portion of the chamfer 212 of the distal end chamfer block 222, extends from the distal edge 225 of the side chamfer block 220 to the cutting guide slot 205. Another tapered cutting guide slot 207, one surface of which is co-planar with a portion of the chamfer 213, extends from the distal edge 222 to the cutting guide slot 204. The side chamfer block 220 is also provided with an aperture 202 for affixing a screw to the medial or lateral femur F.

The angular orientation of the cutting slots 204 and 205 and guide slots 206 and 207 is designed to be consistent with the angular orientation of respective surfaces of the femoral prosthesis intended to be in mating engagement with the surfaces resected using such cutting slots 204 and 205 and guide slots 206 and 207. Assuming the flat prepared surface at the distal end of the femur F which is contacted by the third surface 218 of the distal end chamfer block 222 is vertical (as shown in FIG. 15), the angle between vertical and the various slots could, by way of example and not limitation, be as follows:

cutting slot 204—90° to 95° from vertical
cutting slot 205—93° to 96° from vertical
guide slot 206—45° from vertical
(i.e. included angle 135° from vertical)

Referring to FIGS. 17, 18 and 19, that portion of FIG. 17 in solid lines is the anterior/posterior femoral resection guide 217 described with reference to FIGS. 15 and 16. That portion of FIG. 17 shown in dashed lines, is an anterior/posterior femoral resection block generally designated by the numeral 237 and shown in greater detail in FIGS. 18 and 19. Following completion of the resecting performed using the side femoral resection block 217 and its side chamfer block 220 and distal end chamfer block 222, there remains to be resected anterior and posterior portions at the partially resected distal end of the femur F. This may be accomplished by use of an anterior/posterior femoral resection block 237 which is designed to be engaged to the distal end chamfer block 222.

The anterior-posterior femoral resection block 237 is provided with first and second co-planar wall sections 233 and 234 which are separated by an angular cavity defined by angled wall surface 231 disposed at an angle extending inwardly from planar surface 234 and angled wall surface 232 disposed at an angle extending inwardly from planar wall surface 233. The angled wall surface 231 and 232 are perpendicular to one another and are sized to engage the chamfered surfaces 212 and 213 when the co-planar surfaces 233 and 234 are engaged to the distal edge 225 of the anterior-posterior femoral resection guide 217. The anterior/posterior femoral resection block 237 is provided with apertures 238 and 239 which are aligned respectively with the threaded apertures 214 and 215 of the distal end chamfer block 222. The anterior/posterior femoral resection block 237 may be secured to the distal end chamber block 222 by bolts extending through the respective holes 238 and 239 and threadedly engaged to the threaded apertures 214 and 215. The anterior/posterior femoral resection block 237 is provided with an anterior cutting guide surface 235 and a posterior cutting guide surface 236 for guiding movement of a cutting saw when the anterior/posterior femoral resection block 237 is fastened to the distal end chamfer block 222.

Figure 22:
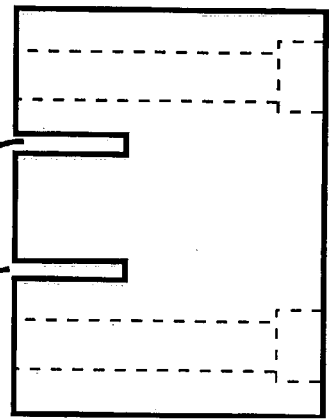
FIG. 22 is an anterior view of the notch block of FIG. 20.
Figure 21:
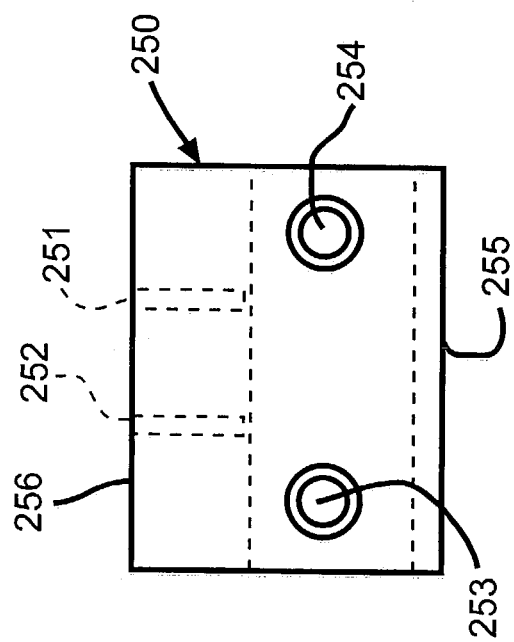
FIG. 21 is a distal view of the notch block of FIG. 20.
Figure 20:
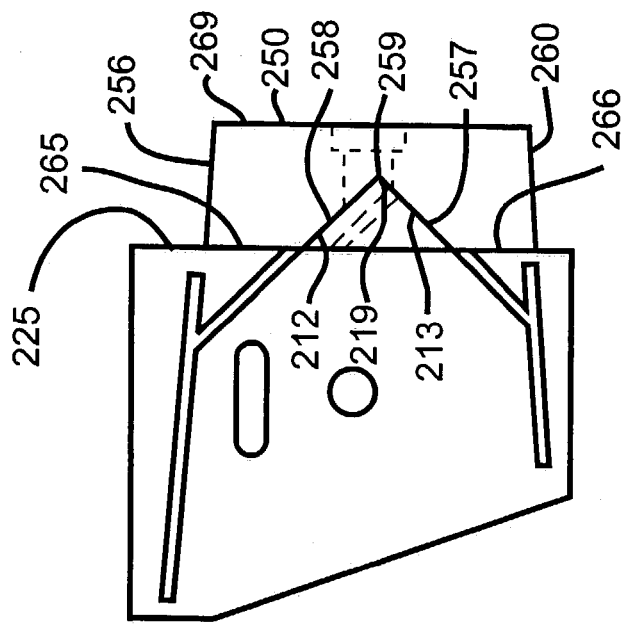
FIG. 20 is a side view of an anterior/posterior chamfer femoral guide in combination with a femoral notch block.

Referring to FIGS. 20, 21 and 22, there is provided a femoral notch block 250 which can be used with the anterior/posterior femoral resection guide block 217 following cutting of the anterior and posterior portions of the femur with the anterior/posterior femoral resection block 237. The femoral notch block 250 attaches over the distal end chamfer block 222 and has first and second flat wall sections 265 and 266 for engagement with the distal edge 225 of the side chamfer block 220. An angled cavity extends inwardly from the plane defined by surfaces 265 and 266 and is defined by a first tapered surface 257 extending inwardly at an angle from wall surface 266 and tapered surface 258 extending at an angle inwardly from surface 265. The surfaces 257 and 258 are perpendicular to one another and meet at an apex 259. The angled surfaces 257 and 258 engage respectively the angled surfaces 213 and 212 of the distal end chamfer block 222. The femoral notch block 250 has an anterior surface 256 and a posterior surface 260 extending from opposite ends of a front face 269 toward the femur F. The femoral notch block 250 has apertures 253 and 254 extending inwardly from the front face 269 and aligned with the apertures 214 and 215 and may thus be secured to the distal end chamfer block 222 by screws extending through the apertures and 253 and 255 and engaged to the threaded recesses 214 and 215.

The femoral notch block 250 has a pair of spaced apart cutting guide slots 251 and 252 extending inwardly from the anterior surface 256 of the femoral notch block. The sizing and placement of the guide slots 251 and 252 is such that a cutting saw guide through each of such guide slots 251 and 252 will meet the previous cut from a cutting saw guided through a cutting slot 209 thereby forming a notch in the intracondylar area of the distal femur. This provides a notch for the posterior stabilizer of a femoral prosthesis positioned thereon.

Referring to FIGS. 23–26, there is shown a modified anterior/posterior side loading sizer guide 400 which permits proper alignment of an aperture for guiding the positioning of a guide pin such as the guide pin 200 of the embodiment of FIGS. 12–14 without the necessity of using a wedge such as the wedge 196 provided in the embodiment of FIGS. 12–14.

Figure 24:
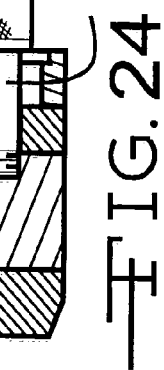
FIG. 24 is a sectional view taken through line 24—24 in FIG. 23.
Figure 25:
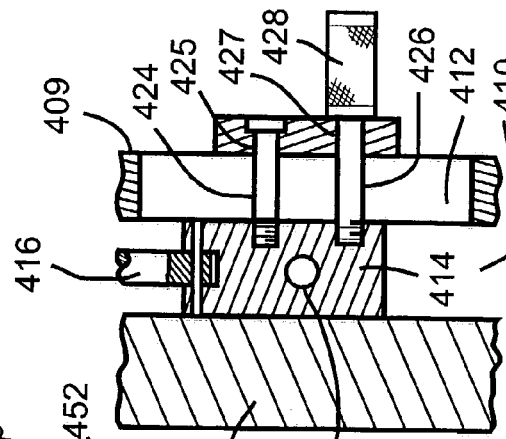
FIG. 25 is a sectional view taken through line 25—25 in FIG. 23.
Figure 23:
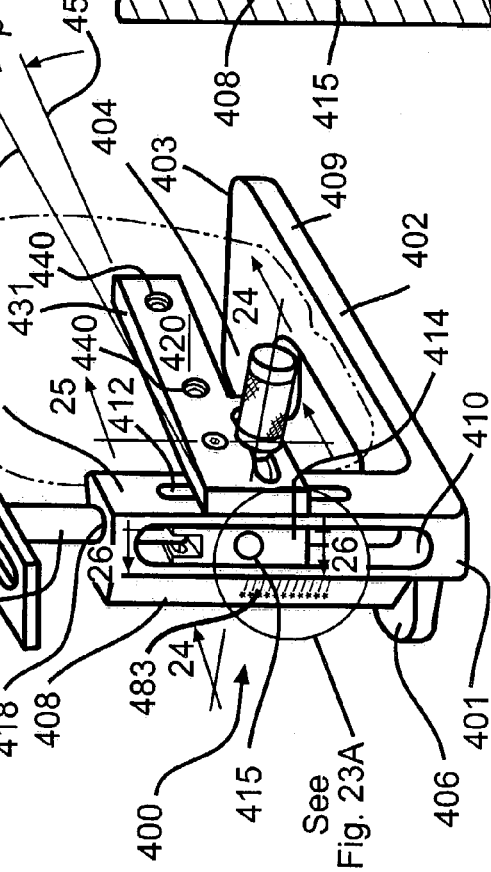
FIG. 23 is a perspective view of another embodiment of femoral anterior/posterior side loading sizer guide.
Figure 23A:
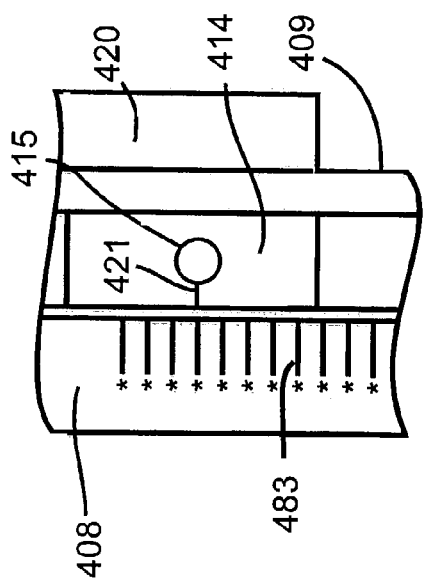
FIG. 23A is an enlargement of that portion of the sizer guide within the circle identified as "See FIG. 23A" shown in FIG. 23.
Figure 26:
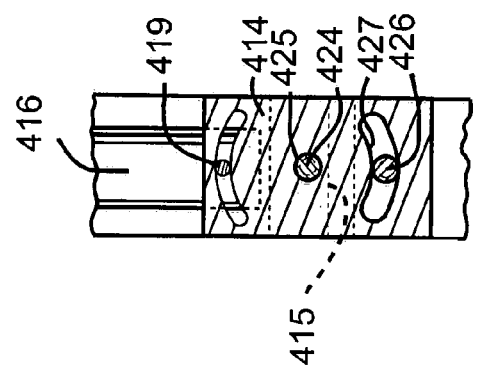
FIG. 26 is a sectional view taken through line 26—26 in FIG. 23.

The anterior/posterior side loading sizer guide 400 shown in FIGS. 23–25 includes a base 402 having a central portion with a first foot 406 at a first end 401 and a second foot 404 at the opposing second end 403 and cooperating with the central portion to define a U-shaped structure. Extending upwardly from the end of the base 402 in the area of the first end 401 is an upstanding support member 408 which, preferably, is integral and unitary with the base 402 and disposed substantially at right angles thereto. The base 402 and the upstanding support member 408 have a common front surface 409. The upstanding support member 408 has a first elongated slot 410 extending throughout a major portion thereof and positioned with the opening of the slot 410 looking from the first end 401 toward the second end 403. The upstanding support member 408 is also provided with a second elongated slot 412 positioned at 90° to the first slot 410, extending rearwardly from the front surface 409 and joining with the opening defined by the first slot 410. Positioned in the first slot 410 is a slideable guide member 415 having a guide alignment hole 415 extending therethrough in a direction substantially parallel to the direction of the front surface 409 of the sizer guide 400. Access to the slideable guide member 414 from the front surface 409 may be had through the second slot 412.

The slideable guide member 414 is mounted on the end of a plunger rod 416 which extends through an aperture 418 in the upper end of the upstanding support member 408. The plunger rod 416 is snuggly received in the aperture 418 for slideable movement therein. The upper end of the plunger rod 416 has an enlarged nut 417 for gripping and moving the plunger rod 416 and the slideable guide member 414 upwardly or downwardly in the first slot 410. The slideable guide member 414 is slideable in the first slot 410 but in close relationship therewith so that the walls of the first slot 410 prevent rotational movement of the slideable guide member 414 about the axis of the plunger shaft 416; however, the walls defining opposing sides of the first slot 410 are parallel to the front surface 409 and are also parallel to one another thereby permitting a rotational movement of the guide member 414 in such first slot 410 about an axis perpendicular to such walls. The connection between the guide member 414 and the plunger shaft 416 is on a pivot pin 419 which permits such rotation relative to the plunger 416. Extending through the slideable guide member 414 along an axis parallel to the front surface 409 is a guide alignment hole 415. In the area of the upstanding support member 408 on the opposite side of the first slot 410 from the front surface 409 is a calibrated scale 483. Extending radially outwardly from the guide alignment hole 415 is a mark 421 etched or otherwise formed in the slideable guide member 414 which, upon alignment with a specific mark on the scale 483, will provide the surgeon with the anterior/posterior dimension of the distal end of the femur F.

An anterior femoral stylus 495 having an elongated slot 481 is affixed to the plunger rod 416 immediately below the flat headed nut 417. Upon loosening of the flat headed nut 417, the anterior femoral stylus 495 may be adjusted inwardly or outwardly and rotationally to engage the desired area of the femur F.

Secured to the front surface 409 of the upstanding support member 408 is a distal condylar arm 420 which is pivotally mounted for angular movement relative to the base 402 and the first and second foot portions 404 and 406 thereof upon which the posterior surface of the femur F is intended to rest. The distal condylar arm 420 is secured to the guide member 414 by a first threaded screw 424 which extends through an aperture 425 of the distal condylar arm 420 and a second threaded screw 426 which extends through an arcuate slot 427 and having a rotatable handle 428 extending therefrom. Upon loosening of the handle 428, the distal condylar arm 420 may be pivoted to the desired angular displacement relative to the surface of the first and second foot portions 404 and 406 of the base 402 upon which the posterior side of the femur F is positioned. The angular displacement is represented by the angle B in FIG. 23 as the angle between a line 450 parallel to the plane defined by the surfaces of the foot portions 404 and 406 upon which the posterior surface of the femur is intended to rest and the line 452 representing the angle of the upper surface 431 of the distal condylar arm 420.

As is the case in the embodiment of FIGS. 12–14, the condylar arm 420 has a flat engagement surface 422 which is intended to engage the resected surface of the distal end of the femur F. The flat engagement surface 422 is parallel to the front surface 409 and parallel to the axis of the guide alignment hole 415. The flat upper surface 431 is also parallel to the axis of the guide alignment hole 419. A pair of apertures 440 extend through the condylar 420. Pins or screws may be introduced through such apertures 440 in order to firmly engage the condylar arm 420 and the rest of the sizer guide 400 to the distal end of the femur F prior to drilling a guide pin such as the guide pin 200 of the embodiment of FIG. 12 into the femur F using the guide alignment hole 415. The holes in which such pins or screws are received in the distal end of the femur may be formed by a drill having a stop extending through such apertures 440. Following drilling through the guide alignment hole 415 and positioning of the guide pin 200, the sizer guide 400 may be removed and the side femur resection guide 217 (FIGS. 15 and 16) may be positioned over the guide pin 200 and secured to the distal end of the femur F by means of screws extending through the apertures 214 and 215 of the distal end chamfer block 222.

In use, the anterior/posterior side loading sizer guide 400 is positioned with the foot members 404 and 406 contacting the posterior femoral condyles when in flexion and with the engagement surface 422 of the distal condylar arm 420 engaged to the resected surface of the distal end of the femur F. By loosening the rotatable handle 428, the surgeon is then able to move the distal condylar arm 420 to obtain the correct angular rotational position for the patient involved, for example, 3°, 5°, 7° etc. Such angular movement of the distal condylar arm 420 will carry with it an angular movement to the guide member 414 thereby obtaining a positioning for the axis of the guide aperture 415 suitable for receiving a guide pin similar to the guide pin 200 of the embodiment of FIG. 12. Upon such positioning, the axis of the aperture will be parallel to the line 452.

The instrumentation of the present invention permits resectioning of the proximal end of a tibia and distal end of a femur with minimal disruption of or damage to the soft tissue and with many of the resection cuts being able to be performed medially or laterally as a result of the unique design of the instrumentation. A significant factor in minimizing damage to the soft tissue resides in the feature of the instruments which permits resectioning to be done either laterally or medially.

Modifications will be readily apparent to those skilled in the art. Accordingly, the scope of the present invention should be limited only by the scope of the claims appended hereto.

We claim:

1. A method for resectioning the proximal end of a tibia comprising the steps of
    (a) providing a tibial resection guide having
        (i) an engagement surface following a contoured path permitting engagement with two spaced apart portions of said tibia, one of said portions being in the vicinity of an anterior cortex and the other of said portions being in the vicinity of either a medial cortex adjacent a medial collateral ligament or a lateral cortex adjacent a lateral collateral ligament;
(ii) an opposed surface spaced from said engagement surface;
(iii) a first end between said engagement surface and said opposed surface;
(iv) a second end between said engagement surface and said opposed surface;
(v) a proximal surface; and
(vi) a slot for receiving and guiding the path of a saw extending therethrough, said slot extending between said opposed surface and said engagement surface and permitting positioning of said saw medially in the vicinity of a medial collateral ligament or laterally in the vicinity of a lateral collateral ligament;
(b) positioning said resection guide with said engagement surface in the area of said tibia proximal end and in contact with said tibia in the area of said anterior cortex and either said medial cortex or said lateral cortex and with said slot being substantially perpendicular to the mechanical axis of said tibia;
(c) displacing said medial collateral ligament or said lateral collateral ligament with said first end; and
(d) resecting said tibia proximal end with a saw extending through said slot.

2. The method according to claim 1 further including the step of displacing a patella tendon with said second end prior to said step of resecting.

3. A tibial resection guide for use in resectioning a proximal end of a tibia while preventing damage to medial collateral ligaments positioned adjacent said tibia proximal end comprising:
(a) an engagement surface following a contoured path permitting engagement with two spaced apart portions of said tibia, one of said portions being in the vicinity of an anterior cortex and the other of said portions being in the vicinity of a medial cortex adjacent a medial collateral ligament;
(b) an opposed surface on an opposite side from said engagement surface, said opposed surface or an extension thereof meeting said engagement surface (i) at a first location to define a first end and (ii) at a second location to define a second end;
(c) a proximal surface adapted for positioning in the vicinity of said tibia proximal end;
(d) a slot for receiving and guiding the path of a saw extending therethrough, said slot extending between said opposed surface and said engagement surface and permitting positioning of said saw medially in the vicinity of said medial collateral ligament;
(e) a medial collateral engagement surface in the vicinity of said first end for displacing said medial collateral ligament while said saw extends through said slot; and
(f) a patella engagement surface in the vicinity of said second end for displacing the patella tendon while said medial collateral engagement surface is displacing said medial collateral ligament.

4. A tibial resection guide for use in resectioning a proximal end of a tibia while preventing damage or lateral collateral ligaments positioned adjacent said tibia proximal end comprising:
(a) an engagement surface following a contoured path permitting engagement with two spaced apart portions of said tibia, one of said portions being in the vicinity of an anterior cortex and the other of said portions being in the vicinity of a lateral cortex adjacent a lateral collateral ligament;
(b) an opposed surface on an opposite side from said engagement surface, said opposed surface or an extension thereof meeting said engagement surface (i) at a first location to define a first end and (ii) at a second location to define a second end;
(c) a proximal surface adapted for positioning in the vicinity of said tibia proximal end;
(d) a slot for receiving and guiding the path of a saw extending therethrough, said slot extending between said opposed surface and said engagement surface and permitting positioning of said saw laterally in the vicinity of said lateral collateral ligament;
(e) a lateral collateral engagement surface in the vicinity of said first end for displacing said lateral collateral ligament while said saw extends through said slot; and
(f) a patella engagement surface in the vicinity of said second end for displacing the patella tendon while said lateral collateral surface is displacing said lateral collateral ligament.

5. A one-piece tibial resection guide for use in resectioning a proximal end of a tibia while preventing damage to medial collateral ligaments positioned adjacent said tibia proximal end comprising:
(a) an engagement surface following a contoured path permitting engagement with two spaced apart portions of said tibia, one of said portions being in the vicinity of an anterior cortex and the other of said portions being in the vicinity of a medial cortex adjacent a medial collateral ligament;
(b) an opposed surface on an opposite side from said engagement surface, said opposed surface or an extension thereof meeting said engagement surface (i) at a first location to define a first end and (ii) at a second location to define a second end;
(c) a proximal surface adapted for positioning in the vicinity of said tibia proximal end;
(d) a slot for receiving and guiding the path of a saw extending therethrough, said slot extending between said opposed surface and said engagement surface and permitting positioning of said saw medially in the vicinity of said medial collateral ligament;
(e) a medial collateral engagement surface in the vicinity of said first end for displacing said medial collateral ligament while said saw extends through said slot; and
(f) a patella engagement surface in the vicinity of said second end for displacing the patella tendon while said medial collateral engagement surface is displacing said medial collateral ligament.

6. A one-piece tibial resection guide for use in resectioning a proximal end of a tibia while preventing damage or lateral collateral ligaments positioned adjacent said tibia proximal end comprising:
(a) an engagement surface following a contoured path permitting engagement with two spaced apart portions of said tibia, one of said portions being in the vicinity of an anterior cortex and the other of said portions being in the vicinity of a lateral cortex adjacent a lateral collateral ligament;
(b) an opposed surface on an opposite side from said engagement surface, said opposed surface or an extension thereof meeting said engagement surface (i) at a first location to define a first end and (ii) at a second location to define a second end;
(c) a proximal surface adapted for positioning in the vicinity of said tibia proximal end;
(d) a slot for receiving and guiding the path of a saw extending therethrough, said slot extending between said opposed surface and said engagement surface and permitting positioning of said saw laterally in the vicinity of said lateral collateral ligament;

(e) a lateral collateral engagement surface in the vicinity of said first end for displacing said lateral collateral ligament while said saw extends through said slot; and (f) a patella engagement surface in the vicinity of said second end for displacing the patella tendon while said lateral collateral surface is displacing said lateral collateral ligament.

* * * * *